US010329678B2

(12) United States Patent
Bouchez et al.

(10) Patent No.: US 10,329,678 B2
(45) Date of Patent: Jun. 25, 2019

(54) METHOD AND DEVICE FOR CONTROLLING THE ACTIVITY OF A BIOELECTROCHEMICAL SYSTEM COMPRISING BOTH A BIOANODE AND A BIOCATHODE

(71) Applicant: Institut national de Recherche en Sciences et Technologies pour l'Environnement et l'Agriculture (IRSTEA), Antony (FR)

(72) Inventors: Théodore Bouchez, Villemoisson (FR); Arnaud Bridier, Fougeres (FR); Elie Le Quemener, Narbonne (FR)

(73) Assignee: Institut national de Recherche en Sciences et Technologies pour l'Environnement et l'Agriculture (IRSTEA), Antony (FR)

( * ) Notice: Subject to any disclaimer, the term of this patent is extended or adjusted under 35 U.S.C. 154(b) by 9 days.

(21) Appl. No.: 15/515,393

(22) PCT Filed: Sep. 29, 2015

(86) PCT No.: PCT/FR2015/052585
§ 371 (c)(1),
(2) Date: Mar. 29, 2017

(87) PCT Pub. No.: WO2016/051064
PCT Pub. Date: Apr. 7, 2016

(65) Prior Publication Data
US 2017/0218530 A1 Aug. 3, 2017

(30) Foreign Application Priority Data
Sep. 30, 2014 (FR) ...................... 14 59281

(51) Int. Cl.
C25B 15/02 (2006.01)
C25B 1/02 (2006.01)
(Continued)

(52) U.S. Cl.
CPC ............. *C25B 15/02* (2013.01); *C12M 41/48* (2013.01); *C25B 1/02* (2013.01); *C25B 9/08* (2013.01);
(Continued)

(58) Field of Classification Search
None
See application file for complete search history.

(56) References Cited

U.S. PATENT DOCUMENTS 4,652,501 A * 3/1987 Bennetto ........... H01M 8/04186
429/2
2006/0234110 A1* 10/2006 Bergel ................ H01M 4/8892
429/401

FOREIGN PATENT DOCUMENTS

CN 102925492 2/2013
WO 2009008709 1/2009

OTHER PUBLICATIONS

Rozendal R A et. al"Principle and Perspectives of Hydrogen Production Through Biocatalyzed Electroysis".
(Continued)

*Primary Examiner* — Alix E Eggerding
(74) *Attorney, Agent, or Firm* — Ipsilon USA, LLP

(57) ABSTRACT

A method for controlling the activity of an electrochemical device (11) comprising a bioanode (3) and a biocathode (6) immersed in an electrolyte (10A, 10C) containing microorganisms, the anode compartment (8) and cathode compartment (9) being separated by at least one membrane (14), optionally a reference electrode, a difference in potential being applied between the bioanode (3) and the biocathode
(Continued)

(6), or between the bioanode and the reference electrode, characterised in that the operation of the device is governed by a dual control: —a priority control of the difference in potential between the bioanode and the biocathode, or between the bioanode and the reference electrode, between a minimum limit value allowing the development of an electroactive biofilm at the bioanode and a maximum limit value lower than the oxidation potential of said biofilm, and—a secondary control, when the first control is in place, optimising the Faradaic efficiency of the biocathode. A device allowing said method to be carried out.

18 Claims, 7 Drawing Sheets

(51) Int. Cl.
  *C25B 9/08* (2006.01)
  *C12M 1/36* (2006.01)
  *C25B 9/10* (2006.01)
  *H01M 8/16* (2006.01)

(52) U.S. Cl.
  CPC ............... *C25B 9/10* (2013.01); *H01M 8/16* (2013.01); *H01M 2300/0025* (2013.01)

(56) References Cited

OTHER PUBLICATIONS

Marianna Villano et al: "Electrochemically Assisted Methane Production in a BBiofilm Reactor".
Search Report dated Dec. 15, 2015.

* cited by examiner

METHOD AND DEVICE FOR CONTROLLING THE ACTIVITY OF A BIOELECTROCHEMICAL SYSTEM COMPRISING BOTH A BIOANODE AND A BIOCATHODE

RELATED APPLICATION

This application is a National Phase of PCT/FR2015/052585, filed on Sep. 29, 2015 which in turn claims the benefit of priority from French Patent Application No. 14 59281, filed on Sep. 30, 2014, the entirety of which are incorporated by reference.

BACKGROUND

Field of the Invention:

The present invention relates to the electrochemical field, and more particularly to electrochemical methods implementing bioelectrochemical devices, i.e. electrochemical devices, at least one of the electrodes of which makes contact with microorganisms.

Description of Related Art

Bioelectrochemical devices are recent. The study of biological anodes in the context of bio batteries started in the noughties in experimental devices in which the cathode was often abiotic. Sometimes, air cathodes that could optionally be biological were however used.

Bioelectrochemical devices have been subject to an increasing amount of attention over the last few years with a view to studying how to take advantage of and bioconvert organic material, which is in particular obtained from organic waste, in microbial electrolyzers. These bioelectrochemical devices require a biological anode (also called a bioanode) to be coupled to a biological cathode (also called a biocathode) and require a good kinetic coordination of the biological activities of the anode and cathode. Often, these activities are not well synchronized. Thus, the activity of one of the bioelectrodes in general takes precedence and may cause, in the circuit, potentials or currents that are detrimental to the correct operation of the other bioelectrode.

To the present day, biocathodes for electrosynthesis have practically never been studied in a system also including a bioanode. However, in future industrial waste biorefining applications, the use of both a bioanode and a biocathode will be necessary.

OBJECTS AND SUMMARY

A first aim of the invention is therefore to mitigate the drawbacks of existing methods by making provision to regulate variations in the respective activities of the bioelectrodes, i.e. to coordinate the microbial activities both on a bioanode and on a biocathode of an electrochemical device, the anodic and cathodic compartments of which contain microorganisms.

To this end, the present invention proposes a method for regulating the activity of an electrochemical device including an anode and a cathode that are submerged in an electrolyte placed in an anodic compartment and a cathodic compartment, respectively, these compartments being separated by at least one membrane or connected to each other by a salt bridge, the device optionally including a reference electrode, a potential difference being applied between the anode and the cathode, or between the anode and the reference electrode; characterized in that the electrolyte of the anodic compartment, and the electrolyte of the cathodic compartment contain microorganisms in suspension or in the form of one or more biofilms, the electrodes thus being called the bioanode and biocathode, respectively, and in that the operation of the device is controlled via a dual regulation:

a first regulation, called the priority regulation, of the potential difference between the bioanode and the biocathode or between the bioanode and the reference electrode, between a minimal limit value allowing an electroactive biofilm to develop on the bioanode and a maximum limit value that is lower than the oxidation potential of said biofilm; and once the first regulation has been implemented, a second regulation, called the subsidiary regulation, that optimizes the faradaic efficiency of the biocathode.

Conventionally, in microbial electrosynthesis experiments, since the reduction reactions take place on the biocathodes, prior-art electrochemical devices have merely implemented a regulation of the current or of the potential at the cathode. When a bioanode is present, this type of regulation may lead to a large increase in the potential at the anode, which leads to excessive oxidation and thus inactivation of the electroactive biomass on contact with this electrode.

Now, the inventors have observed that it is surprisingly and unexpectedly preferable to employ, on start, a strategy for regulating the potential at the anode. Once an oxidation microbial activity has been achieved at the anode such that a current level that is judged to be sufficient is obtained in the circuit, it becomes necessary to regulate the current density and/or the potential at the biocathode in order to allow a suitable biological activity at the cathode (regulation of the current or the potential in ranges compatible with the activity of the anode). The method according to the invention therefore first takes into account the variation in the biological activity at the anode, via the priority regulation of the potential at the bioanode (priority law).

Throughout the present document, the expressions coulombic efficiency, coulombic yield, faradaic yield and faradaic efficiency are equivalent and have the same meaning from the electrochemical point of view.

The current density (in $A/m^2$) at the bioanode or at the biocathode corresponds to the current per unit area of the electrode of which it is question.

By "bioanode" and "biocathode" what is meant here is electrodes that are submerged in an electrolyte in contact with microorganisms and an electrolyte. These microorganisms may be organized into biofilms in direct contact with the electrodes, walls of the reactor and/or be in suspension in the electrolyte. Throughout the text the terms anode or bioanode, and cathode or biocathode will be used interchangeably.

Advantageously, while maintaining the regulation of the potential at the bioanode, the optimization of the activity of the biocathode with a view to producing particular chemical species is automatically controlled depending on physicochemical parameters measured in the cathodic compartment, i.e. parameters such as the concentration of one or more chemical species in the electrolyte or in the gaseous atmosphere nearby the biocathode, or the rate of gas production at the biocathode.

The chemical species measured in the cathodic compartment is for example dihydrogen (resulting from an abiotic effect of electrolysis of water and meaning that the current must be decreased to improve the operation of the biocathode) or methane (which means that electro-methanogensis is occurring at the biocathode).

According to one advantageous embodiment of the invention, while maintaining the first regulation of potential difference controlling the biological activity at the bioanode, the second regulation controls the optimization of the current density at the biocathode with a view to producing particular chemical species at the biocathode.

This optimization of current density of the biocathode may be achieved:

according to a first variant: by way of an electronic device allowing the current at the biocathode to be set directly, and/or by way of a voltage generator or a potentiostat that allows the potential of the bioanode, of the biocathode and/or the potential difference between the bioanode and biocathode to be varied, preferably with a precision of a few millivolts; or according to a second variant: by varying the ratio of the active area of the bioanode to the active area of the biocathode.

In this second variant, the ratio of the active area of the bioanode to the active area of the biocathode may be varied:

either by varying the submerged area of the bioanode and/or the biocathode, these variations in the submerged area of the bioanode and/or biocathode possibly being obtained by varying the level of the electrolyte in the anodic compartment and/or in the cathodic compartment, or by moving the bioanode and/or the biocathode in the electrolyte;

or by modifying the number of bioanodes in the anodic compartment and/or by modifying the number of biocathodes in the cathodic compartment: i.e. by introducing one or more new bioanodes (biocathodes, respectively) into the anodic compartment (cathodic compartment, respectively), or removing one or more bioanodes and/or biocathodes, in the case where the compartment(s) already comprise(s) a plurality thereof.

In the case where the anodic and cathodic compartments comprise a plurality of electrodes (bioanodes or biocathodes, respectively), these electrodes are of course all connected to the same electrical circuit of the electrochemical device.

According to another embodiment, the activity of the biocathode may be regulated using physico-chemical parameters at the anodic compartment. More particularly, while maintaining the regulation of the potential at the bioanode, the activity of the biocathode is then optimized with a view to producing particular chemical species by regulating chemical parameters at the anodic compartment, i.e. parameters such as the concentration of one or more chemical species in the electrolyte or in the gaseous atmosphere nearby the bioanode.

This chemical species is advantageously a non-fermentable molecule such as an organic acid or its salt and is preferably chosen from acetate, lactate or propionate.

By way of exemplary priority regulation, when the bioanode, such as an electrode made of carbon, is submerged in an aqueous electrolyte having a pH of about 7, the maximum value of the potential difference between the bioanode and a standard hydrogen electrode, called reference electrode, is such that the potential of the bioanode is lower than or equal to 1 V with respect to said reference electrode and preferably lower than 0.5 V with respect to said reference electrode so as to prevent electrolysis of the water.

The present invention also relates to an electrochemical device for carrying out the method described above, allowing currents and/or potentials at the cathode to be controlled depending on the variation in the biological activity at the anode.

More specifically, the electrochemical device according to the invention comprising:

an anode and a cathode that are submerged in an electrolyte placed in an anodic compartment and a cathodic compartment, respectively, these compartments being separated by at least one membrane or connected to each other by a salt bridge, the electrolyte of the anodic compartment containing microorganisms, as does the electrolyte of the cathodic compartment, the electrodes thus being called the bioanode and biocathode, respectively;

optionally a reference electrode; and means allowing a potential difference to be applied between the bioanode and the biocathode, or between the bioanode and the reference electrode, and means for controlling this potential difference;

is characterized in that it comprises means allowing the faradaic efficiency of the biocathode to be optimized, the optimization being automatically controlled depending on physico-chemical parameters measured at the cathodic compartment and/or at the anodic compartment.

The membrane may be an ion exchange membrane: cation exchange membrane, anion exchange membrane, proton exchange membrane; or as a variant may be an osmosis membrane.

This electrochemical device may also comprise sensors or probes placed in the electrolyte and/or in the gaseous atmosphere nearby the bioanode or biocathode, respectively, said sensors or probes measuring physico-chemical parameters at the anodic compartment and/or the cathodic compartment, i.e. parameters such as the concentration of one or more chemical species.

The electrochemical device according to the invention may also comprise means allowing the level of the electrolyte in at least one of the compartments to be varied (for example by means of a pump connected to an inlet and an outlet of the corresponding compartment) and/or allowing the bioanode and/or the biocathode to be moved in the electrolyte.

BRIEF DESCRIPTION OF THE DRAWINGS

The invention will be better understood on reading the following description of exemplary embodiments, given with reference to the appended drawings, in which.

DETAILED DESCRIPTION

EXAMPLES

Example 1

Figure 1:
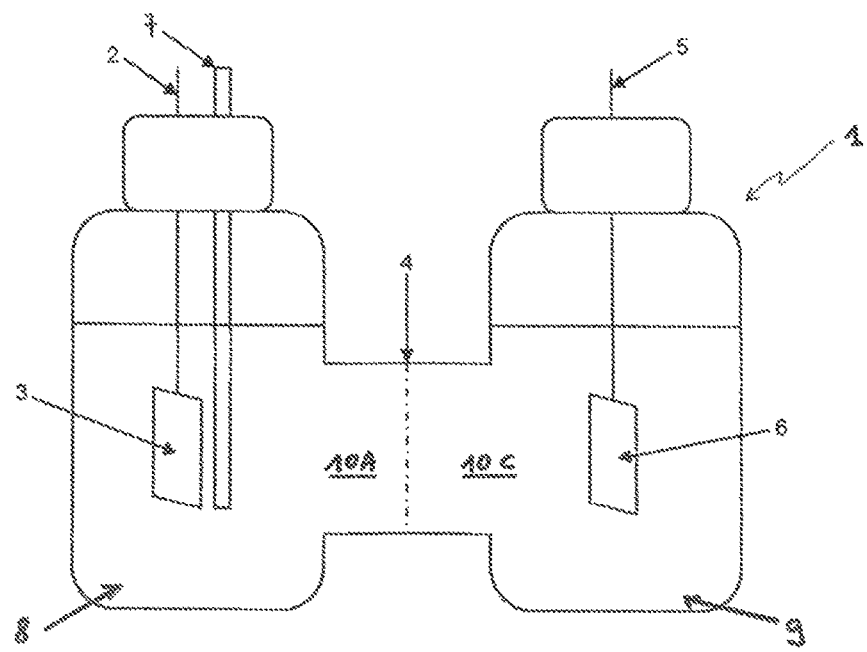
FIG. 1 is a cross-sectional schematic of one embodiment of an electrochemical device according to the invention.

The electrochemical device 1 shown in FIG. 1 is a dual-compartment electrolyzer including a bioanode 3 and a biocathode 6. The two compartments, i.e. the anodic compartment 8 and the cathodic compartment 9, consist of glass containers of 1.5 L total volume separated by a cation exchange membrane 4 (CEM, Fumasep® FKE, Germany). The electrolyte 10A, 10C used corresponds to the biochemical methane potential (BMP) medium (according to standard NF EN ISO 11734) buffered with 8 g/L of carbonates. The substrate used is acetic acid in an amount of 600 mg/L. The base material of the bioanode is a 4 cm×4 cm piece of carbon fabric (Paxitech®, France) and it is connected to the electric circuit by a platinum wire 2. The material of the biocathode is a 4 cm×4 cm sheet of stainless steel (Outokumpu®, 254 SMO) connected to the electric circuit by a steel rod 5.

The bioanode was "precultivated" on acetic acid in biological sludge, this allowing a biofilm containing electroactive bacteria to be obtained on the surface of the carbon fabric. The cathodic compartment 9 may optionally be inoculated with an acetogenic bacteria culture prepared from an anaerobic waste-processing microbial consortium (biocathode).

The anode 3 is initially polarized to +0.158 V with respect to a saturated calomel reference electrode 7 (SCE) by means of a potentiostat (Biologic®, France, VMP3, software package EC-Lab) (priority law). When the current density reaches 5 A/m$^2$, the potentiostat is programmed to limit the current density to this value. This allows the activity of the cathode to be regulated (subsidiary law). Lastly, if the potential at the anode exceeds +0.2 V versus SCE, the potentiostat is then set up to switch back to the potential control mode and to maintain this value in order to preserve the biological activity of the bioanode (priority law). This regulation is illustrated in FIG. 3 for the first 16 days of the experiment.

Figure 3:
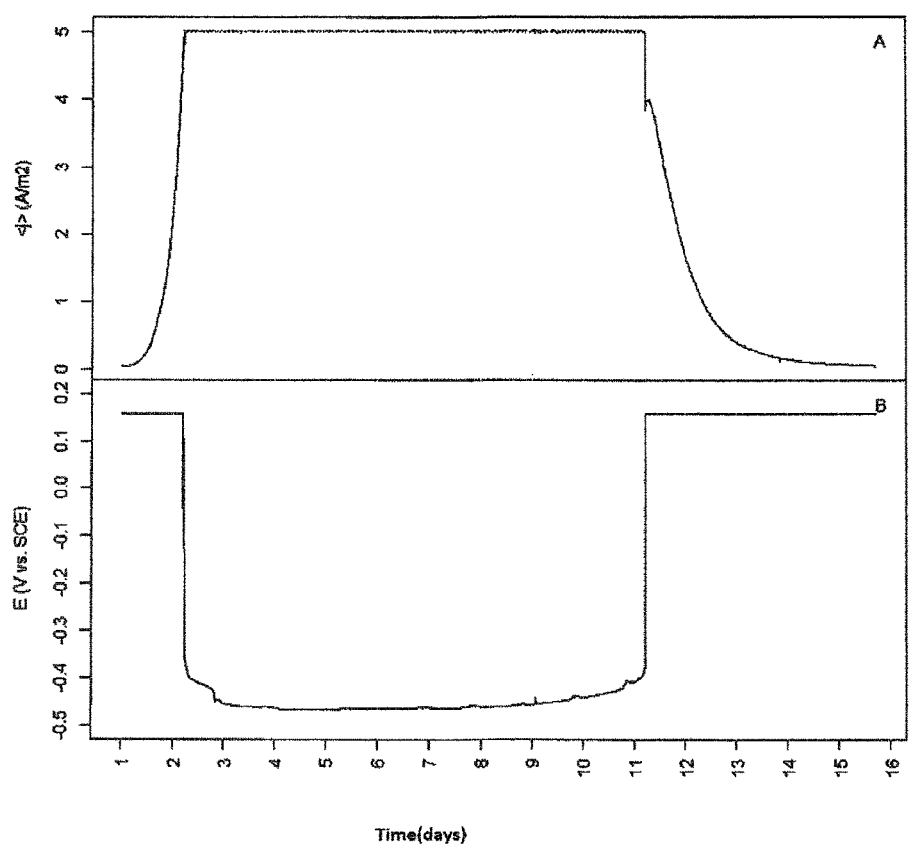
FIG. 3 shows the curves of current density (FIG. 3A) and potential (FIG. 3B) of example 1.

FIG. 3 shows, for the first 16 days of the experiment, curves of the current density (FIG. 3A) and of the potential (FIG. 3B) of the bioanode, the latter being measured with respect to the saturated calomel reference electrode 7. At the start of the experiment, the current rapidly increases with the development of the electroactive biofilm at the anode. The current is then regulated to 5 A/m$^2$ in order to optimize the production yield of volatile fatty acids (VFAs) at the cathode (subsidiary law). In the last phase, the current decreases with the depletion of the substrate, while the priority law again sets the potential of the anode 3.

Throughout the experiment, samples are taken in which concentrations of volatile fatty acids and lactate are measured by ion chromatography (DIONEX DX 120, ION-PAC® ICE-AS1 column (9×250 mm)). The eluents used are heptafluorobutyric acid (0.4 mmol/L) and tetrabutylammonium hydroxide (TBAOH, 5 mmol/L). The concentrations of formate, acetate, lactate, propionate, butyrate and valerate are thus measured in a range extending from 10 mg/L to 500 mg/L. The compositions of the gaseous atmospheres of the anodic and cathodic compartments are measured by gas phase chromatography (Varian CP 4900). The three columns of the instrument allow the proportions of the following gases to be measured: $O_2$, $N_2$, $CH_4$, $CO_2$, $H_2$, $H_2S$ and $NO_2$.

Figure 4:
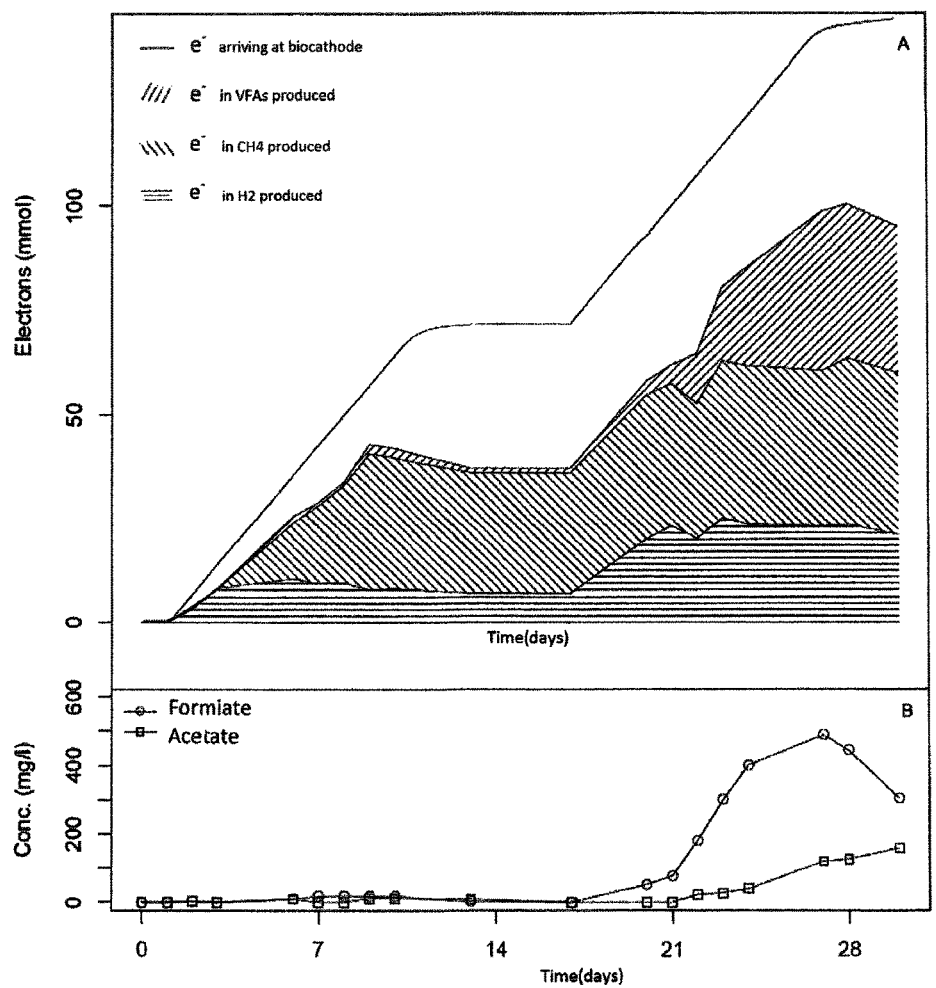
FIG. 4 depicts, for example 1, the electron tally at the biocathode of example 1 with the cumulative amounts of volatile fatty acids (VFAs), methane ($CH_4$) and dihydrogen ($H_2$) (FIG. 4A) and the volatile fatty acids measured in the cathodic compartment (FIG. 4B)

The experiment was carried out for 30 days, with two injections of substrate into the anodic compartment 8 (600 mg/L of acetic acid) on days 0 and 15. Three pilots were launched in parallel under the same conditions with inoculation at the cathode (biocathode) and three other control pilots were launched without inoculation at the cathode. The behaviors of the three pilots with inoculation turned out to be very similar throughout the experiment, one thereof was stopped on day 15 to allow observation of the electrodes by microscopy. The production tally of the biocathode of one of these pilots is shown in FIGS. 4 (parts A and B).

FIG. 4A shows the electron tally for a biocathode 6 with inoculation. The upper curve indicates the number of electrons arriving at the biocathode. The cumulative amounts of volatile fatty acids (VFAs), methane ($CH_4$) and dihydrogen ($H_2$), measured in electrons equivalents, are indicated by the hatched areas. FIG. 4B shows in detail the volatile fatty acid concentrations measured in the cathodic compartment 9. Formate and acetate are the main acids produced. The concentrations measured for the other acids (lactate, propionate, butyrate and valerate) are zero and are therefore not shown in this figure.

During the first phase of the experiment (days 1 to 15), hydrogen ($H_2$) and methane ($CH_4$) are mainly produced in the cathodic compartments having received an inoculation whereas the pilots without inoculation of the cathodic compartment produce only hydrogen. The faradaic efficiency at the biocathode is then 60% with 53% of the electrons used to produce methane (FIG. 4A).

On day 15, the second substrate is injected into the anodic compartment 8 and 10 mmol/L of 2-bromo-ethane sulfonate (BES) are injected into the cathodic compartment 9 to inhibit methanogenesis. During the second phase, volatile fatty acids such as formate and acetate are mainly produced, as well as small amounts of hydrogen and methane. The faradaic efficiency at the cathode then reaches 80%. 29% of the electrons have been used to produce acetate. The maximum rate of production of acetate recorded during this phase is 11 g of acetate/m$^2$/day. Moreover 18%, 19% and 13% of the electrons are used to produce formate, hydrogen and methane respectively (FIG. 4). Traces of caprylate have also been detected by gas chromatography-mass spectrometry analyses.

The faradaic efficiency at the anode during the experiment is 85% on average.

Observations of the bioanodes and biocathodes under confocal laser scanning microscope at 15 days and 30 days reveal a substantial microbial colonization of the two bioelectrodes.

Example 2

Optimization of the current at the biocathode by regulation of potential difference.

In this exemplary embodiment, the bioelectrochemical reactor is a dual-compartment electrolyzer such as that shown in FIG. 1 and is operated under the same experimental conditions as example 1. The embodiment of the method of the present invention here consists in modulating the potential difference between the anode 3 and the cathode 6 by virtue of the use of a potentiostat to control the current at the biocathode.

Figure 5:
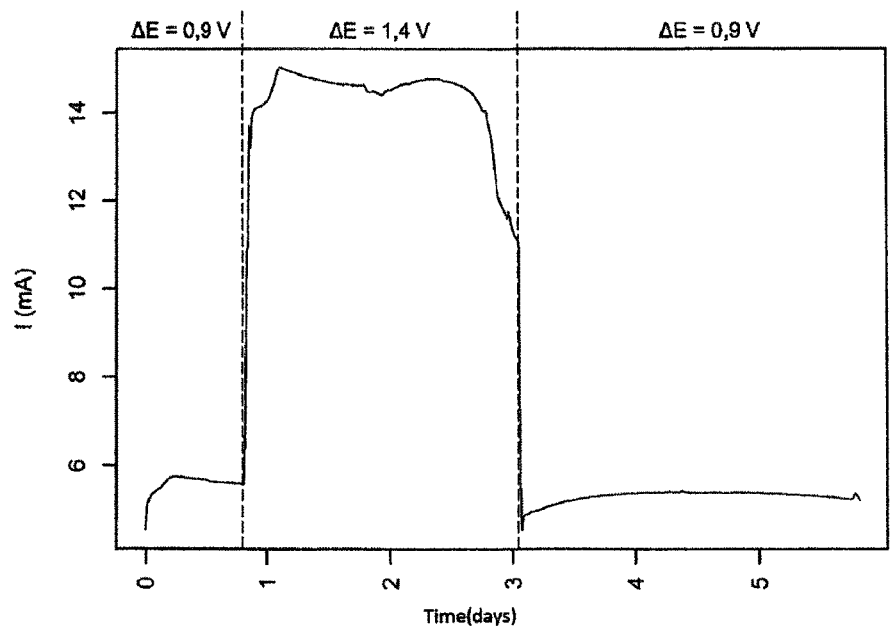
FIG. 5 shows the current in the electrochemical device according to example 2 as a function of time.

FIG. 5 shows an example of the current flow through the bioelectrochemical reactor over time. The two different observed current levels (days 0-1 and 3-6 on the one hand, days 1-3 on the other hand) correspond to two potential differences applied between the bioanode and the biocathode. The applied potential difference was either 0.9 V (days 0-1 and 3-6) or 1.4 V (days 1-3).

More particularly, in the first phase of the experiment, the potential difference is set to 0.9 V between the bioanode and the biocathode. After about one day of experiment, the potential difference is increased to 1.4 V between the two electrodes. The obtained curve of current as a function of time confirms that this variation in potential difference causes an increase in current, from about 5-6 mA to 15 mA. After 4 days, the potential difference is returned to 0.9 V and is correlated with a drop in the current to a value very close to its initial value (about 5 mA). Controlling the potential difference between the bioanode and biocathode therefore allows the magnitude of the current flowing through the bioelectrochemical reactor to be regulated and therefore the activity of the biocathode to be regulated.

Example 3

Optimization of the current at the biocathode by movement of the bioanode in the electrolyte.

Figure 6:
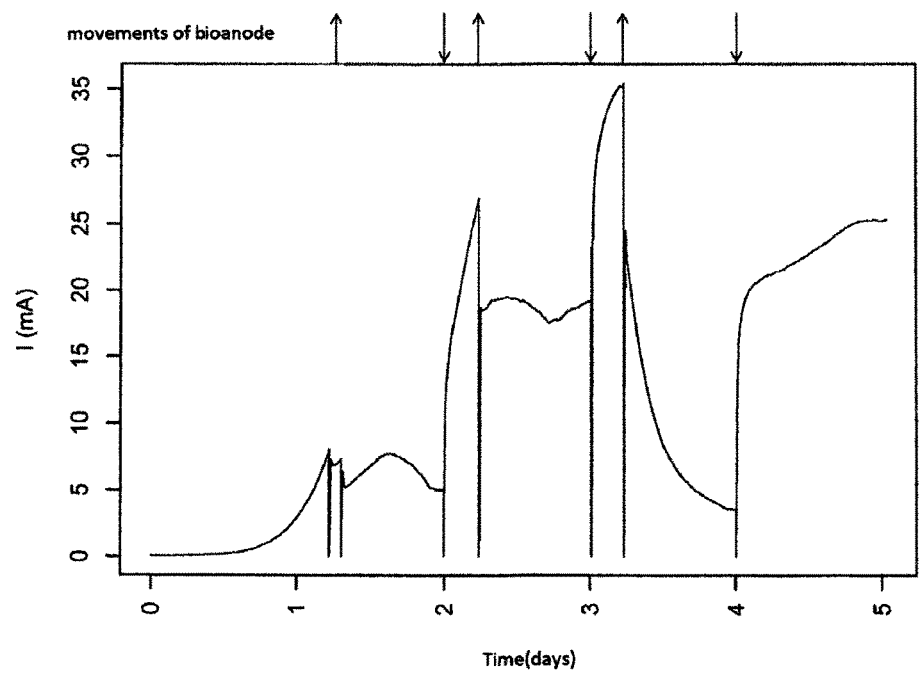
FIG. 6 shows the current in the electrochemical device according to example 3 as a function of time, and the movements of the bioanode in the electrolyte.

In this exemplary embodiment, the bioelectrochemical reactor is a dual-compartment electrolyzer such as that shown in FIG. 1 and is operated under the same experimental conditions as example 1. The invention here consists in modulating the area of bioanode submerged in the electrolyte in order to make the current at the biocathode vary. FIG. 6 shows an example of the current flow through the bioelectrochemical reactor over time. The movements of the bioanode in the compartment are indicated by the arrows. Initially, the bioanode 3 is completely submerged in the electrolyte 10A. The upward pointing arrows indicate that half of the electrode is raised out of the electrolyte and the downward pointing arrows indicate that the electrode is again completely submerged. It may be seen that the abrupt variations in current clearly correspond to the variations in the submerged area of the bioanode.

Specifically, in this exemplary embodiment, the submerged area of the bioanode is modified a plurality of times during the experiment. After a little more than one day, half of the bioanode 3 is raised out of the electrolyte, decreasing the submerged area by half. In parallel to this, a decrease in the current from 8 mA to about 5 mA is observed. On the second day, the bioanode is again completely submerged in the electrolyte and then an abrupt increase in the current is observed. The experiment is thus repeated 3 times and allows, on each variation in the submerged area of the bioanode, a correlated variation in the current at the biocathode to be observed. Controlling the submerged area of the bioanode therefore allows the current of the bioelectrochemical reactor to be regulated and therefore the activity of the biocathode to be regulated.

Example 4

Regulation of the current at the biocathode depending on concentration in COD (chemical oxygen demand) at the anode.

In this exemplary embodiment, the bioelectrochemical reactor is a dual-compartment electrolyzer such as that shown in detail in FIG. 1 and is operated under the same experimental conditions as example 1 with the exception of the nature of the substrate fed to the anode. Specifically, in this embodiment, the anodic compartments of two reactors were supplied with biodegradable waste, a complex substrate of 63 g/L total COD, the composition of which in volatile fatty acids and lactic acid is shown in table 1 below.

TABLE 1

|  | Conc. (g/L) |
| --- | --- |
| Lactic acid | 10.52 |
| Formic acid | 0.00 |
| Acetic acid | 0.38 |
| Propionic acid | 1.28 |
| Butyric acid | 5.32 |
| Valeric acid | 0.00 |

Figure 7:
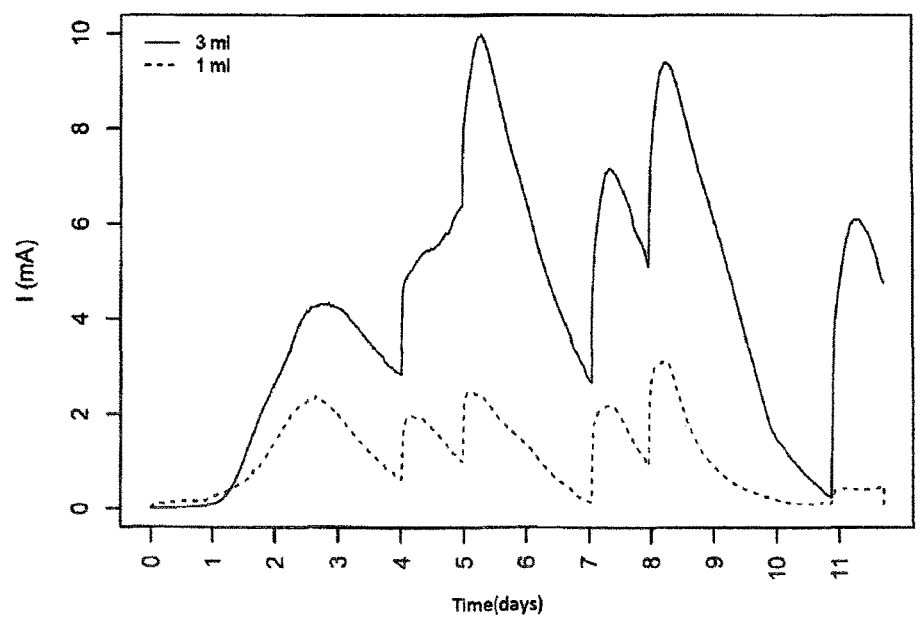
FIG. 7 shows the current in the two electrochemical devices according to example 4 as a function of time.

FIG. 7 shows the obtained curves of current as a function of time. The dashed curve corresponds to the reactor the anodic compartment 8 of which received 1 mL of substrate on days 0, 4, 5, 7, 8 and 11. The solid curve corresponds to the reactor the anodic compartment 8 of which received 3 mL of substrate on days 0, 4, 5, 7, 8 and 11.

Figure 8:
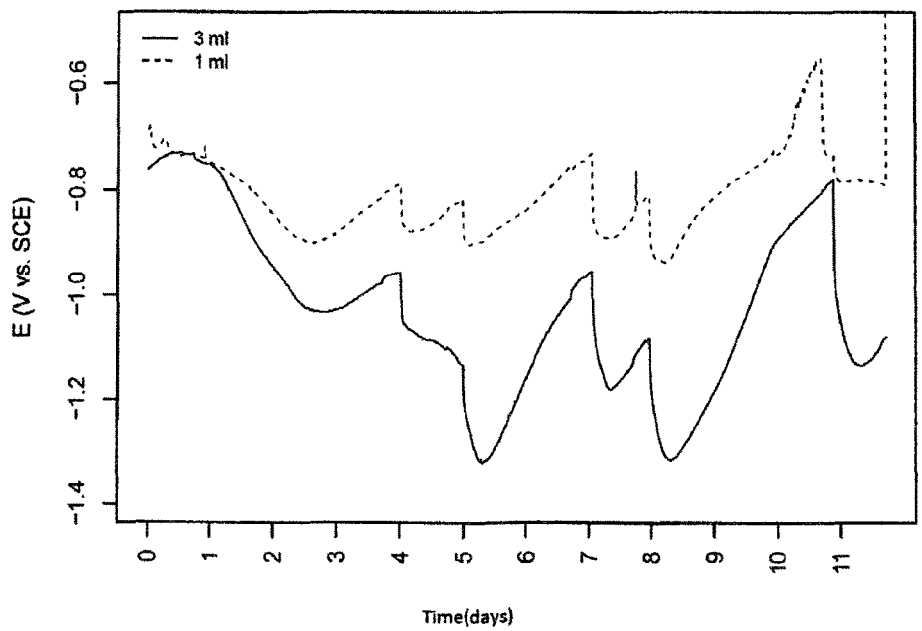
FIG. 8 shows the current in two electrochemical devices according to example 4 as a function of time.

The least supplied reactor received 31.5 mg/L/d of COD on average and the second 94.5 mg/L/d of COD on average. This difference in substrate concentration allowed a different current to be obtained for each reactor since the average current obtained for the reactor supplied with 1 mL of substrate was 1.1 mA, whereas the average current obtained for the reactor supplied with 3 mL of substrate was 4.3 mA (FIG. 7). Regulating the substrate concentration at the bioanode therefore allows the current of the bioelectrochemical reactor to be regulated and therefore the activity of the biocathode to be regulated, as illustrated by the potentials measured at the biocathodes: see FIG. 8, which shows the potentials of the biocathodes of the two bioelectrochemical reactors over time. These potentials are measured with respect to saturated calomel reference electrodes (SCE). The dashed curve corresponds to the reactor that was supplied with 1 mL of substrate on days 0, 4, 5, 7, 8 and 11. The solid curve corresponds to the reactor that was supplied with 3 mL of substrate on days 0, 4, 5, 7, 8 and 11.

Example 5

Optimization of the activity of the biocathode by regulation of chemical parameters.

Figure 9:
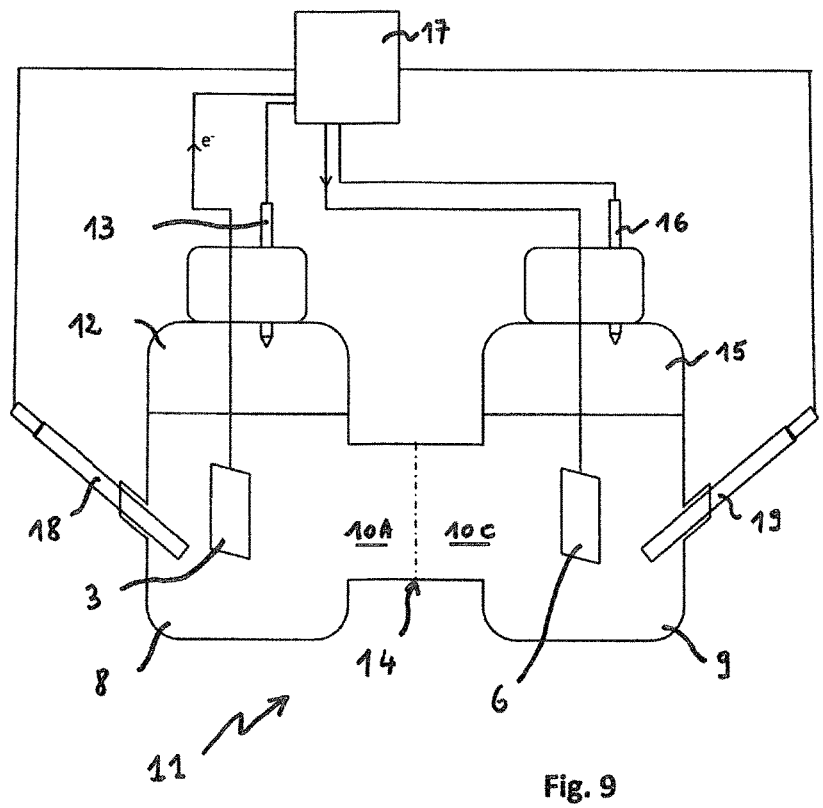
FIG. 9 is a general schematic of an electrochemical device according to invention including various physico-chemical sensors.

This example implements an electrochemical device including physico-chemical sensors. This electrochemical device 11, which is shown schematically in FIG. 9, includes an anode 3 and a cathode 6 that are connected to an electronic device 17 comprising a potentiostat. A membrane 14, for example a cation exchange membrane, separates the anodic compartment 8 from the cathodic compartment 9 enclosing the electrolyte 10A, 10C.

Various sensors or probes may be integrated into the two compartments in order to follow the variation in physico-chemical parameters of the system: for example, a gas sensor 13 is placed in the gaseous atmosphere 12 of the anodic compartment and a probe 18 is submerged in the liquid electrolyte 10A of the anodic compartment 8. Likewise, a gas sensor 16 is placed in the gaseous atmosphere 15 of the cathodic compartment and a probe 19 is submerged in the electrolyte 10C of the cathodic compartment 9.

While maintaining the regulation of the potential at the bioanode, the activity of the biocathode is optimized by regulating chemical parameters of the anodic compartment 8, i.e. parameters such as the concentration of one or more chemical species in the electrolyte 10A or in the gaseous atmosphere 12 nearby the bioanode, pH, etc. The presence of various integrated sensors/probes in the two compartments allows the variation in the physico-chemical parameters of the system to be followed directly. Depending on the value of these parameters, the electronic device 17 may then optimize the operation of the biocathode by adjusting the current of the system, the electrical potential, etc.

Example 6

Figure 2:
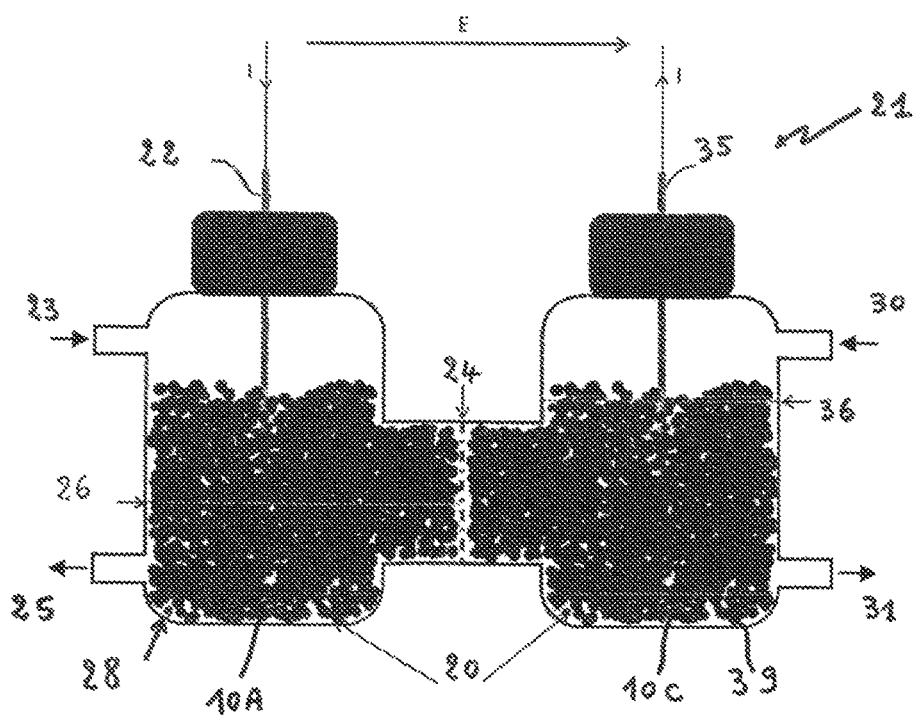
FIG. 2 is a cross-sectional schematic of another embodiment of an electrochemical device according to the invention.

FIG. 2 schematically shows another embodiment of an electrochemical device according to the invention.

In this exemplary embodiment, the electrochemical device 21 is a dual-compartment electrolyzer including a bioanode 22 and a biocathode 35 that are formed from graphite granules 20 connected to the exterior electric circuit by graphite rods. The anodic and cathodic compartments 28, 39 are separated by a cation exchange membrane 24 (CEM). The anodic compartment 28 includes an inlet 23 and an outlet 25 for the electrolyte 10A, which inlet and outlet are for example connected to pumping means (not shown). Likewise, the cathodic compartment 39 includes an inlet 30 and an outlet 31 for the electrolyte 10C, which inlet and outlet may be connected to pumping means (not shown) that are independent from the pumping means connected to the anodic compartment.

This device allows the level 26 of the electrolyte 10 in the anodic compartment and the level 36 of the electrolyte 10C in the cathodic compartment, and therefore the volume of electrolyte in each of these compartments, to be independently modulated, and thus the ratio of the active (i.e. submerged) areas of the two bioelectrodes to be controlled.

In the case where the current (I) is set, this modulation allows the potential difference (E) between the two bioelectrodes to be varied. This makes it possible, initially, during the start-up of the system, to obtain a potential at the anode that is compatible with the instigation of electroactive biological activity. Subsequently, this allows the biosynthesis reactions at the cathode to be controlled, regulating its potential.

In the case where the potential difference (E) between the two bioelectrodes is set, this regulating system allows the electrical current (I) to be modulated, and this will have a direct influence on the carbonic production efficiencies of various molecules, allowing the efficiencies of conversion of electrons into molecules of interest to be optimized.

Example 7

Optimization of current by regulation of potential difference (ΔE) in a dual-compartment electrolyzer including electrodes formed from graphite granules.

In this exemplary embodiment, the electrochemical device 21 is a dual-compartment electrolyzer such as that shown in FIG. 2, including a bioanode 22 and a biocathode 35 that are formed from graphite granules 20 connected to the exterior electric circuit by graphite rods. The anodic and cathodic compartments 28, 39 are separated by a cation exchange membrane 24 (CEM). The anodic compartment 28 includes an inlet 23 and an outlet 25 for the electrolyte 10A, which inlet and outlet are for example connected to pumping means (not shown). Likewise, the cathodic compartment 39 includes an inlet 30 and an outlet 31 for the electrolyte 10C, which inlet and outlet may be connected to pumping means (not shown) that are independent from the pumping means connected to the anodic compartment.

Figure 10:
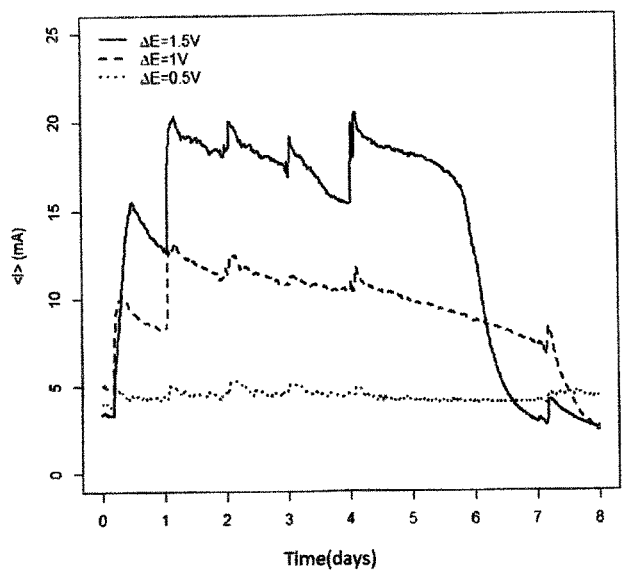
FIG. 10 shows curves of the current variation as a function of time in three devices according to the invention operating with various potential differences between the anode and cathode.

The embodiment of the method of the present invention here consists in modulating the potential difference between the anode 22 and the cathode 35 by virtue of the use of a potentiostat to control current. FIG. 10 shows an example of the current flow over time through three bioelectrochemical reactors operated under the same conditions for three applied potential differences: 0.5 V (dotted curve), 1 V (dashed curve) and 1.5 V (continuous line). At the time t=0 days, the substrate (acetate at a final concentration of 600 mg/L) is added and the current increases for the three reactors. The maximum currents obtained reach values of 5, 13 and 20 mA for the applied potential differences of 0.5, 1 and 1.5 V, respectively, confirming that the measured current increases as a function of the increase in the potential difference applied between the granular biocathode and bioanode.

Controlling the potential difference between the bioanode and biocathode therefore allows the magnitude of the current flowing through the dual-compartment bioelectrochemical reactor including electrodes formed from graphite granules to be regulated and therefore the activity of the biocathode to be regulated.

Example 8

Figure 11:
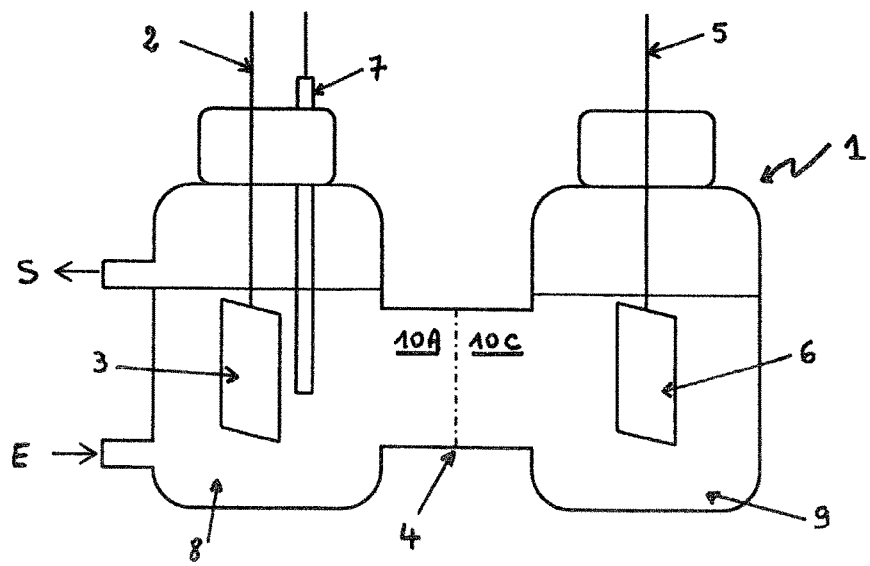
FIG. 11 is a general schematic of a variant electrochemical device according to the invention in which electrolyte is continuously supplied to the anodic compartment.

In this exemplary embodiment, the electrochemical device, schematically shown in FIG. 11, is a dual-compartment electrolyzer including a bioanode and a biocathode and a system for supplying and drawing off the liquid phase. More particularly, in this example, the anodic compartment includes an inlet E and an outlet S for the electrolyte, which inlet and outlet are connected to pumping means (not shown) allowing electrolyte to be continuously supplied to this compartment.

According to this embodiment, the anodic compartment of a reactor has been continuously supplied with biodegradable waste (from the substrate composition presented in table 1 of example 4) by virtue of a pump allowing the flow rate entering to be regulated, and of an overflow system allowing a constant level of liquid to be preserved within the anodic compartment maintained at a volume of 1 L.

Figure 12:
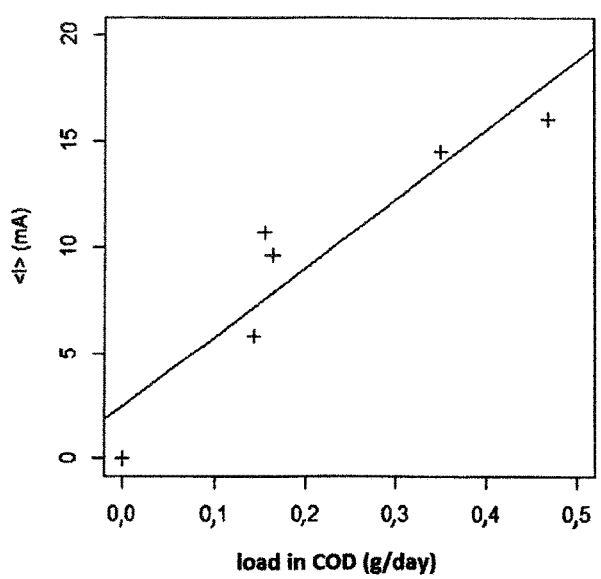
FIG. 12 shows the correlation between the magnitude of the current in the circuit of the device in FIG. 11 and the daily load in COD (chemical oxygen demand) in the electrolyte supplied to the anodic compartment.

The impact of various substrate concentrations in the supply (COD load, COD standing for chemical oxygen demand) on the current has been tested for an average flow rate of 82 mL/day over an average duration of 10 days. The results are shown in FIG. 12.

The observed correlation between the magnitude of the current in the circuit and the flow rate of supplied COD clearly shows that regulation of the flow rate of supplied substrate allows the magnitude of the current to be regulated.

The invention claimed is:
1. A method for regulating the activity of an electrochemical device said device having an anode and a cathode that are submerged in an electrolyte placed in an anodic compartment and a cathodic compartment, respectively, these compartments being separated by at least one membrane or connected to each other by a salt bridge, the device optionally including a reference electrode, said method comprising the steps of:

applying a potential difference between the anode and the cathode, or between the anode and the reference electrode;

wherein the electrolyte of the anodic compartment, and the electrolyte of the cathodic compartment contain microorganisms in suspension or in the form of one or more biofilms, the electrodes thus being called the bioanode and biocathode, respectively, and in that the operation of the device is controlled via a dual regulation including the further steps of:

a first regulation called the priority regulation, of the potential difference between the bioanode and the biocathode or between the bioanode and the reference electrode, between a minimal limit value allowing an electroactive biofilm to develop on the bioanode and a maximum limit value that is lower than the oxidation potential of said biofilm; and once the first regulation has been implemented, a second regulation, called the subsidiary regulation, that optimizes the faradaic efficiency of the biocathode; and wherein, while maintaining the first regulation of potential difference controlling the biological activity at the bioanode, the second regulation controls the optimization of the current density at the biocathode with a view to producing particular chemical species at the biocathode.

2. The method as claimed in claim 1, wherein, while maintaining the regulation of the potential at the bioanode, the optimization of the activity of the biocathode with a view to producing particular chemical species is automatically controlled depending on physico-chemical parameters measured in the cathodic compartment, i.e. parameters such as the concentration of one or more chemical species in the electrolyte or in the gaseous atmosphere nearby the biocathode, or the rate of gas production at the biocathode.

3. The method as claimed in claim 1, wherein the current density at the biocathode is optimized by way of an electronic device allowing the current at the biocathode to be set directly, and/or by way of a voltage generator or a potentiostat that allows the potential of the bioanode, of the biocathode and/or the potential difference between the bioanode and biocathode to be varied.

4. The method as claimed in claim 1, wherein the current density at the biocathode is optimized by varying the ratio of the active area of the bioanode to the active area of the biocathode.

5. The method as claimed in claim 4, wherein the ratio of the active area of the bioanode to the active area of the biocathode is varied by varying the submerged area of the bioanode and/or the biocathode.

6. The method as claimed in claim 5, wherein the variations in the submerged area of the bioanode and/or biocathode are obtained by varying the level of the electrolyte in the anodic compartment and/or in the cathodic compartment.

7. The method as claimed in claim 5, wherein the variations in the active area of the bioanode and/or biocathode are obtained by moving the bioanode and/or the biocathode in the electrolyte.

8. The method as claimed in claim 4, wherein the ratio of the active area of the bioanode to the active area of the biocathode is varied by modifying the number of bioanodes in the anodic compartment and/or by modifying the number of biocathodes in the cathodic compartment.

9. The method as claimed in claim 1, wherein, while maintaining the regulation of the potential at the bioanode, the activity of the biocathode is optimized with a view to producing particular chemical species by regulating chemical parameters in the anodic compartment, i.e. parameters such as the concentration of one or more chemical species in the electrolyte or in the gaseous atmosphere nearby the bioanode.

10. The method as claimed in claim 2, wherein the chemical species is dihydrogen.

11. The method as claimed in claim 2, wherein the chemical species is methane.

12. The method as claimed in claim 9, wherein the chemical species is a non-fermentable molecule such as an organic acid or its salt.

13. The method as claimed in claim 1, wherein when the bioanode, such as an electrode made of carbon, is submerged in an aqueous electrolyte having a pH of about 7, the maximum value of the potential difference between the bioanode and called reference electrode, a standard hydrogen electrode, is such that the potential of the bioanode is lower than or equal to 1 V with respect to the reference electrode and preferably lower than 0.5 V with respect to said reference electrode so as to prevent electrolysis of the water.

14. An electrolyzer for carrying out the method as claimed in claim 1, comprising:

an anode and a cathode that are submerged in an electrolyte placed in an anodic compartment and a cathodic compartment, respectively, these compartments being separated by at least one membrane or connected to each other by a salt bridge, the electrolyte of the anodic compartment containing microorganisms, as does the electrolyte of the cathodic compartment, the electrodes thus being called the bioanode and biocathode, respectively;

optionally a reference electrode; and means allowing a potential difference to be applied between the bioanode and the biocathode, or between the bioanode and the reference electrode, and means for controlling this potential difference;

wherein said electrochemical device comprises means allowing the faradaic efficiency of the biocathode to be optimized, the optimization being automatically controlled depending on physico-chemical parameters measured at the cathodic compartment and/or at the anodic compartment.

15. The electrochemical device as claimed in claim 14, wherein said electrochemical device comprises sensors or probes placed in the electrolyte and/or in the gaseous atmosphere nearby the bioanode or biocathode, respectively, said sensors or probes measuring physico-chemical parameters at the anodic compartment and/or the cathodic compartment, i.e. parameters such as the concentration of one or more chemical species.

16. The electrochemical device as claimed in claim 1, wherein said electrochemical device comprises means allowing the level of the electrolyte in at least one of the compartments to be varied and/or allowing the bioanode and/or the biocathode to be moved in the electrolyte.

17. The method as claimed in claim 3, wherein the current density at the biocathode is optimized by way of an electronic device allowing the current at the biocathode to be set directly, and/or by way of a voltage generator or a potentiostat that allows the potential of the bioanode, of the biocathode and/or the potential difference between the bioanode and biocathode to be varied with a precision of a few millivolts.

18. The method as claimed in claim 12, wherein the chemical species is a non-fermentable molecule such as an organic acid or its salt chosen from acetate, lactate or propionate.

* * * * *